United States Patent [19]

Uchida et al.

[11] Patent Number: 4,752,422
[45] Date of Patent: Jun. 21, 1988

[54] ULTRASONIC HUMIDIFIER

[75] Inventors: Tetsuei Uchida; Tsutomu Uchida; Akio Hirasawa; Susumu Kazama, all of Sanjo, Japan

[73] Assignee: Uchida Manufacturing Co., Ltd., Sanjo, Japan

[21] Appl. No.: 934,850

[22] Filed: Nov. 25, 1986

[30] Foreign Application Priority Data

Jun. 6, 1986 [JP] Japan .............. 61-86910[U]

[51] Int. Cl.[4] .............................. B01F 3/04
[52] U.S. Cl. .................. 261/81; 422/124; 239/58; 261/DIG. 48; 261/DIG. 65
[58] Field of Search ........ 261/DIG. 48, 81, DIG. 65; 422/124; 239/58, 60; 15/257 B

[56] References Cited

U.S. PATENT DOCUMENTS

| | | | |
|---|---|---|---|
| 1,863,883 | 6/1932 | Schneider | 422/124 |
| 1,954,924 | 4/1934 | Engberg et al. | 15/257 B |
| 2,763,395 | 9/1956 | Meek | 239/58 |
| 2,784,465 | 3/1957 | Fuchs | 422/124 |
| 3,930,797 | 1/1976 | Gertz | 422/124 |
| 4,208,012 | 6/1980 | Dutcher | 239/60 |
| 4,268,285 | 5/1981 | Mason | 422/124 |
| 4,272,261 | 6/1981 | Lynch, Jr. et al. | 422/124 |
| 4,554,698 | 11/1985 | Rennecker et al. | 15/257 B |
| 4,617,157 | 10/1986 | Stein et al. | 261/DIG. 65 |
| 4,640,804 | 2/1987 | Mizoguchi | 261/81 |

FOREIGN PATENT DOCUMENTS 56-13557 3/1981 Japan .

OTHER PUBLICATIONS

The American Heritage Dictionary, 2nd College Ed., Apr. 1982, Houghton Mifflin Co.

Primary Examiner—Tim Miles
Attorney, Agent, or Firm—Cushman, Darby & Cushman

[57] ABSTRACT

An ultrasonic humidifier includes a spraying chamber for receiving water received therein, a vibrator adapted to make ultrasonic vibrations, a blower, and a perfume case. Ultrasonic waves are applied to the water by the vibrator to produce a water spray in the form of a mist. The water spray is emitted, by driving the blower, into a room by way of a jet of air scented by the perfume to thereby not only moisten the air in the room but also to give forth a pleasing fragrance. The humidifier further comprises an air-feeding suction port hole formed in one side wall of a body of the humidifier. The perfume case is installed at the air suction port hole so as to be demountable from outside the body of the humidifier.

1 Claim, 2 Drawing Sheets

ULTRASONIC HUMIDIFIER

BACKGROUND OF THE INVENTION

1. Field of the Invention

The present invention relates to an ultrasonic humidifier and, more particularly, to an ultrasonic humidifier which is designed to give out pleasing odors into a room as well as to moisten the internal air thereof.

2. Description of the Prior Art

Conventionally, this type of humidifier is such that, as disclosed in, for example, Japanese Utility Model Examined Publication No. 13557/81, prefumes are disposed in an air feed passage formed between a water tub from which a water spray in the form of a mist is raised and a utility chamber in which a blower is disposed, i.e., in a deeply inward location in the body of the humidifier.

Since perfumes were disposed in such a deeply inward position, therefore, the old humidifier inconveniently must as a whole be disassembled when the perfumes are exchanged for fresh ones in one or two months after installation. Therefore, the perfumes are troublesome to handle.

SUMMARY OF THE INVENTION

The present invention has been made in order to solve the above-mentioned problems and its object is to provide an ultrasonic humidifier which is provided at one side wall of its body with an air-feeding suction port hole, at which perfumes are installed and are easily detachable from outside the body.

A water spray in the form of a mist is produced in a spraying section by the vibrations of a vibrator. To this water spray is fed a jet of air by means of a blower to give out the water spray into a room. When the air in the room is sucked by the blower into the humidifier via an air-feeding suction port hole formed in one side wall of the body of the humidifier, it passes through the perfumes installed at the suction port hole. For this reason, said jet of air is perfumed or scented. Consequently, it not only moistens the internal air of the room but also gives forth pleasing odors to fill the room with fragrance, thereby bringing the users into a peaceful state of mind. When it is desired to replace the perfume producing no fragrance with a fresh one, it is sufficient to simply demount the old perfume installed at the suction port hole, from outside the humidifier and newly install the fresh perfume in substitution for the old one, without disassembling the humidifier and so forth.

DESCRIPTION OF THE PREFERRED EMBODIMENT

Figure 1:
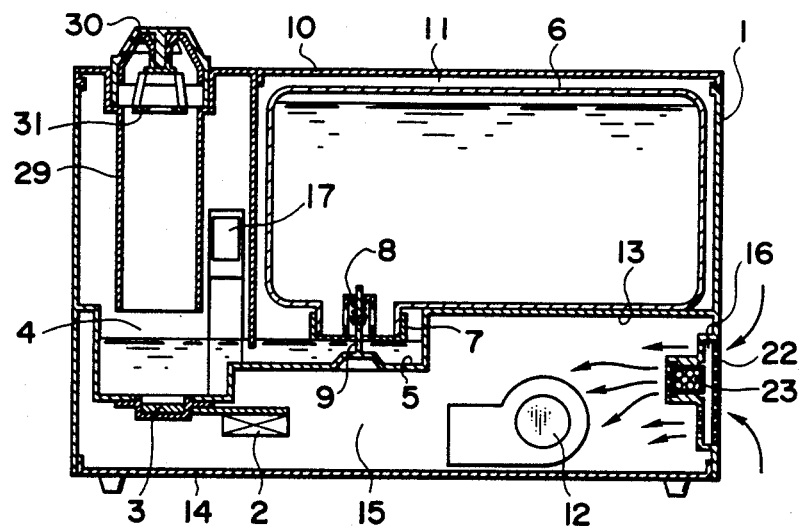
FIG. 1 is a sectional view of an ultrasonic humidifier embodying the present invention.

An ultrasonic humidifier in accordance with the invention will now be described in connection with a preferred embodiment illustrated in the drawings.

Reference numeral 1 denotes a box-like body of the humidifier which is formed of synthetic resin. At one-side portion of the interior of the body there is provided a spraying chamber 4 which is equipped, at its bottom, with an ultrasonic vibrator 3 placed under the control of an ultrasonic vibration circuit. The vibrations of the vibrator 3 are imparted to a specified amount of water stored in the spraying chamber 4 to produce a water spray in the form of a mist.

Reference numeral 5 denotes an auxiliary water tub which is communicated with the spraying chamber 4 and and which is equipped with a push-up rod 9 disposed opposing a valve 8 in a water feed cap 7 for a cartridge type water feed tank or reservoir 6. The auxiliary water tub thus is intended to feed a supplementary water to the spraying chamber 4 from the water feed tank 6. The water feed tank 6 is received within a tank receiving chamber 11 in the body 1 of the humidifier, which is equipped, at its top, with an openable lid member 10 so as not to be seen from outside the humidifier.

Reference numeral 12 denotes a blower installed within a utility chamber 15 which is defined by a partitioning plate 13 constituting a bottom of the spraying chamber 4, auxiliary water tub 5 and tank receiving chamber 11 having the water feed tank placed therein, and a bottom plate 14. The blower 12 is intended to feed the air in the room, which has been sucked from an airfeeding suction port hole 16 formed in that one side wall of the body of the humidifier which constitutes the utility chamber 15, to an air-feeding hole 17 opened into the spraying chamber 4, thereby to cause the water spray produced in the spraying chamber 4 to be given out into the room.

The suction port hole 16 comprises a recessed portion 18 which is inwardly protruded and which is formed with a multiplicity of through holes 19, said recessed portion 18 being detachably provided with a suction cover 22 having laterally elongate holes 20 and being interiorly equipped with a filter 21.

Figure 4:
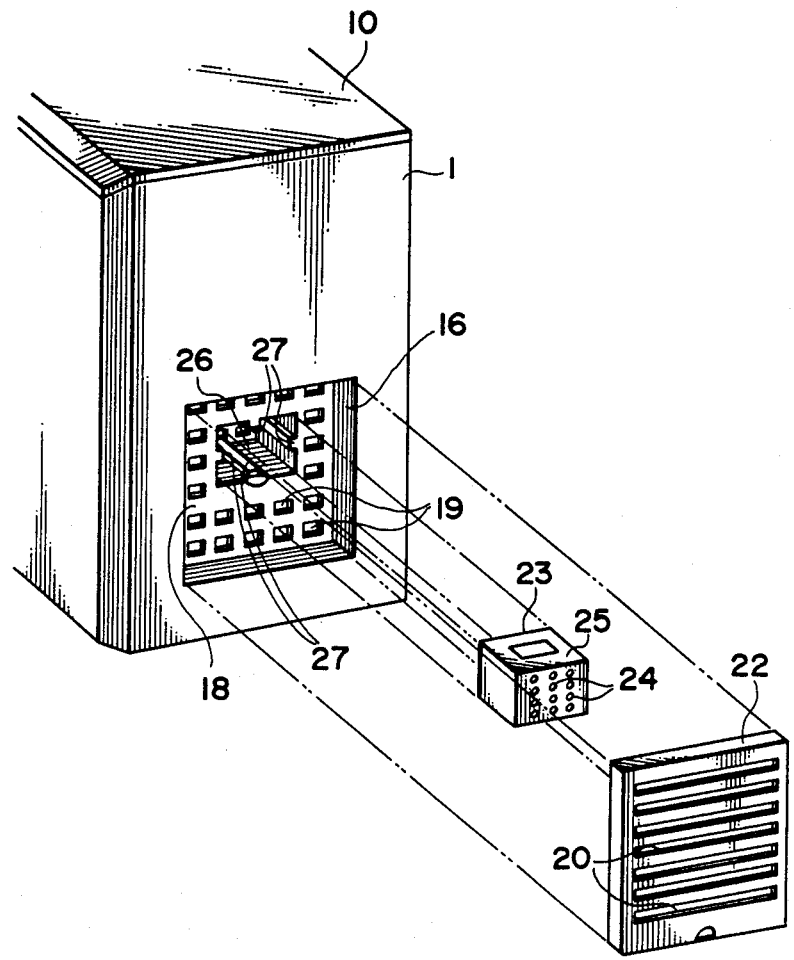
FIG. 4 is a disassembled perspective view of the essential part of the humidifier.

Reference numeral 23 denotes small spherical perfume pieces which have been received in a perfume case 25 shaped like a cubic or regular-quadrangular prism and formed with a multiplicity of vent holes 24. The perfume case 25 is removably received in a receiving section 26 provided by further inwardly protruding of a part of the bottom of the recessed portion 18 disposed at the air-feeding suction port hole 16. Four sides which constitute the inner wall of the receiving section 26 are respectively provided with projections 27 as shown in FIG. 4, to thereby form air flow gaps 28 between those sides and their corresponding outer sides of the perfume case 25.

Since the perfume case 25 is shaped like a cubic or regular-quadrangular prism, the length of its front and back sides is the same as that of its top and bottom sides. Therefore, it is possible to receive the perfume case in a state wherein the former sides are exchanged for the latter sides.

Reference numeral 29 denotes a cylindrical guide member which is downwardly suspended, in the spraying chamber 4, from above the same. The guide member is intended to upwardly guide the water spray having been produced in the spraying chamber 4 so as to emit the same into the room via a cylindrical blowing nozzle 30 rotatably mounted at the top portion of the spraying chamber 4.

Reference numeral 31 denotes a restrictor which is downwardly suspended, within the cylindrical guide member 29, from the cylindrical blowing nozzle 30. The restrictor 31 is intended to remove only large ones of the water particles constituting the water spray coming upwards in the guide member 29, to prevent such large ones from being given out into the room.

The operation of this embodiment will now be described.

The ultrasonic vibrator 3 is now caused to vibrate. The vibrations thereof are imparted to the water in the spraying chamber 4. On the other hand, the blower 12 is driven to operate to feed a jet of air into the spraying chamber 4 under the influence of the ultrasonic vibrations, to thereby produce a water spray. This water spray is given out into the room from the cylindrical guide member 29 by way of the upper blowing nozzle 30. Whereby, the interior of the room is moistened and is brought into a good state of air.

The stream of air carried by the blower is perfumed due to its passing through the suction port hole 16. That is, the air inside the room which is sucked by the driving of the blower 12 first passes through the laterally elongate holes 20 of the suction cover 22 and then, after having its dust for example removed by the filter 21, passes through the through holes 19 of the recessed portion 18, thus flowing into utility chamber 15. Part of the sucked air, however, enters the perfume case 25 in the receiving section 26 via the vent holes 24 and, after having been perfumed therein by the perfume pieces, flows into the utility chamber 15. While being mixed with the remaining sucked air not perfumed, the air passes through the spraying chamber 4 into the room. The air which has entered the room not only moistens the air in the room but also gives forth pleasant odors in the room, giving incitement to the users' five senses to calm their minds, or bring them into a comfortable or peaceful state of mind.

At the time of replacing the perfume pieces 23 because of their ceasing to scent in one or two months after installation, the suction cover 22, first of all, is demounted and, by inserting an operator's fingers, the perfume case 25 is demounted. By thereafter replacing the perfume case 25 as a whole, or the perfume pieces 23 alone in the perfume case 25, it is possible to exchange for fresh perfume in a very simple manner. That is, the perfume pieces can be easily exchanged from outside the humidifier without any troublesome operation of disassembling the entire body of the humidifier as in the prior art. Thus, the perfume pieces are very easy to handle.

Further, since the perfumes 23 are installed not in the entire suction port hole 16 but in a part thereof, it is neither possible that the amount of air sucked is decreased, nor is it necessary to use the blower 12 of large capacity, thus making it possible to use any conventional blower.

Figure 2:
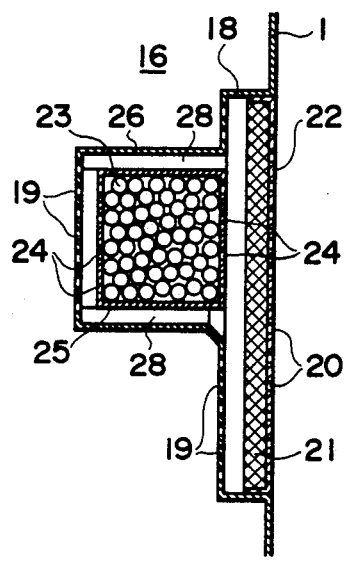
FIG. 2 is an enlarged sectional view of an essential part of the ultrasonic humidifier.
Figure 3:
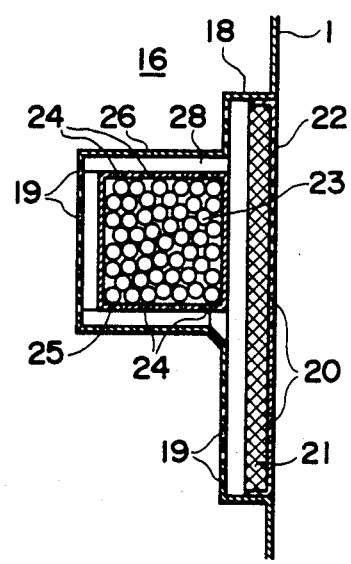
FIG. 3 is an enlarged sectional view of that essential part of the humidifier in which front and back sides of a perfume case are turned 90° about a center thereof to top and bottom sides.

Further, the specified air flow gaps 28 are formed between the outer surface of the perfume case 25 and the inner surface of the receiving section 26, and the perfume case 25 can be received by being freely turned 90° to a state wherein its front and back sides having the vent holes 24 are replaced by its top and bottom sides having no such vent holes 24 and vice versa. So, when it is desired to weaken the scent in the room air, it is sufficient to change the perfume case 25 from a usual state of FIG. 2 to a new state of FIG. 3 wherein its top and bottom sides are vertically erected to replace its front and back sides. That is, it is not necessary to conduct any mechanical operation such as, for example, a varying in capacity of the blower 12 and yet no change occurs in the extent to which the air in the room is moistened, thus to make it possible to weaken or strengthen the scent or perfume only. Where no scent is needed, the perfume case 25 has only to be left demounted.

On the other hand, providing the air flow gaps or passages 28 as stated before makes it possible to cause the air, which is made difficult to flow through the perfume case 25 due to the resistance of the perfume pieces 23, to easily flow therethrough while it is being sucked by the force of the other air flowing from the outside of the perfume case 25 along the vent holes 24 of the back sides thereof into the utility chamber 24. Thus, it is possible to obtain a good flow of scented air.

To summarize the above, according to the invention, the perfume pieces 23 are installed at the suction port hole 16 formed in one side wall of the body 1 of the humidifier, and therefore are easily demountable from outside the humidifier. For this reason, while they not only moisten the air in the room but also give a good fragrance to the users to bring them into a comfortable or peaceful state of mind, they are easily replaceable by fresh perfume pieces, providing a readiness of being employed.

Further, according to the invention, the perfume pieces are received in the perfume case provided, at only front and back sides thereof, with the vent holes. The perfume case is received in the receiving section formed at the suction port hole, in such a manner that the specified air flow gaps are defined between the outer surfaces of its walls of the case and the inner surfaces of the corresponding walls of the receiving section. At this time, the case can be also received by being turned 90° to a state wherein its front and back sides are made horizontal to replace its top and bottom sides, or wherein its top and bottom sides are made vertical to replace its front and back sides. By exchanging, as above, the front and back sides for the top and bottom sides or vice versa, it is possible to weaken or strengthen the fragrance of the perfume without any inconvenience of simultaneously varying the extent of moistening by varying the capacity of the blower. Namely, it is possible to attain a great effect by a very simple operation of interchanging the positions of the front and back sides with those of the top and bottom sides of the perfume case.

What is claimed is:

1. An ultrasonic humidifier for scenting and humidifying air, comprising:
   A housing having entry and exit openings defined therein for allowing air to pass therethrough;
   means in said housing for storing water;
   ultrasonic vibrator means for agitating water from said storing means to produce a spray;
   blower means in said housing for drawing air through said entry opening, past said ultrasonic vibrator means and out through said exit opening, thereby humidifying the air;
   a perfume case having a plurality of vent holes defined in front and back sides thereof; and
   means defined in said housing for receiving said perfume case, so that specified air flow gaps are defined between outer surfaces of the case and inner surfaces of said receiving means, and so that said perfume case may be received in said receiving means in at least four separate positions turned 90° degrees from each other.

* * * * *